(12) United States Patent
Hibner

(10) Patent No.: US 11,439,427 B2
(45) Date of Patent: Sep. 13, 2022

(54) ULTRASONIC SURGICAL INSTRUMENT WITH CLAMP ARM DEFLECTION FEATURE

(71) Applicant: Ethicon LLC, Guaynabo, PR (US)

(72) Inventor: John A. Hibner, Mason, OH (US)

(73) Assignee: Cilag GmbH International, Zug (CH)

( * ) Notice: Subject to any disclaimer, the term of this patent is extended or adjusted under 35 U.S.C. 154(b) by 106 days.

(21) Appl. No.: 16/696,315

(22) Filed: Nov. 26, 2019

(65) Prior Publication Data
US 2020/0179000 A1 Jun. 11, 2020

Related U.S. Application Data

(63) Continuation of application No. 15/200,333, filed on Jul. 1, 2016, now Pat. No. 10,543,014.

(51) Int. Cl.
*A61B 17/32* (2006.01)
*A61B 17/29* (2006.01)

(52) U.S. Cl.
CPC .......... *A61B 17/320092* (2013.01); *A61B 2017/2902* (2013.01); *A61B 2017/2937* (2013.01); *A61B 2017/2939* (2013.01); *A61B 2017/320094* (2017.08); *A61B 2017/320095* (2017.08)

(58) Field of Classification Search
CPC .......... A61B 17/320092; A61B 2017/320094; A61B 2017/320095; A61B 2017/2939; A61B 17/28; A61B 17/29; A61B 17/295
See application file for complete search history.

(56) References Cited

U.S. PATENT DOCUMENTS

| | | | |
|---|---|---|---|
| 5,322,055 A | 6/1994 | Davison et al. |
| 5,758,420 A | 6/1998 | Schmidt et al. |
| 5,873,873 A | 2/1999 | Smith et al. |
| 5,980,510 A | 11/1999 | Tsonton et al. |
| 6,024,750 A | 2/2000 | Mastri et al. |
| 6,325,811 B1 | 12/2001 | Messerly |
| 6,773,444 B2 | 8/2004 | Messerly |

(Continued)

FOREIGN PATENT DOCUMENTS

CN 104582599 A 4/2015

OTHER PUBLICATIONS

International Search Report and Written Opinion dated Aug. 2, 2017 for Application No. PCT/US2017/039485, 15 pages.
(Continued)

*Primary Examiner* — Kathleen S Holwerda
(74) *Attorney, Agent, or Firm* — Frost Brown Todd LLC

(57) ABSTRACT

An apparatus includes a shaft assembly and an end effector. The shaft assembly includes a first tube, a second tube, and a distally projecting tongue. The second tube is coaxially disposed within the first tube. One of the first tube or the second tube is configured to translate relative to the other of the first tube or the second tube. The tongue is fixed to either the first tube or the second tube. The end effector includes an ultrasonic blade and a clamp arm. The clamp arm is pivotally coupled to the tongue. The clamp arm is configured to pivot toward and away from the ultrasonic blade in response to relative translation between the first and second tubes. The tongue is configured to flex relative to the first tube and the second tube in response to the clamp arm grasping tissue.

20 Claims, 13 Drawing Sheets

(56) References Cited

U.S. PATENT DOCUMENTS

| | | |
|---|---|---|
| 6,783,524 B2 | 8/2004 | Anderson et al. |
| 7,336,533 B2 | 2/2008 | Hunter et al. |
| 8,461,744 B2 | 6/2013 | Wiener et al. |
| 8,591,536 B2 | 11/2013 | Robertson |
| 8,623,027 B2 | 1/2014 | Price et al. |
| 8,663,220 B2 | 3/2014 | Wiener et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 9,381,058 B2 | 7/2016 | Houser et al. |
| 9,393,037 B2 | 7/2016 | Olson et al. |
| 10,285,724 B2 | 5/2019 | Faller et al. |
| 10,543,014 B2 | 1/2020 | Hibner |
| 2006/0058825 A1 | 3/2006 | Ogura et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2011/0196286 A1 | 8/2011 | Robertson et al. |
| 2012/0116265 A1 | 5/2012 | Houser et al. |
| 2014/0330298 A1* | 11/2014 | Arshonsky ........... A61B 17/295 606/169 |
| 2015/0141981 A1 | 5/2015 | Price et al. |
| 2015/0245850 A1 | 9/2015 | Hibner et al. |
| 2016/0015419 A1 | 1/2016 | Hibner et al. |

OTHER PUBLICATIONS

US Provisional U.S. Appl. No. 61/410,603, filed Nov. 5, 2010.
U.S. Pat. No. 10,543,014.
Brazil Office Action dated Dec. 10, 2021, for Application No. BR112018077494-4, 4 pages.
Chinese Office Action and Search Report dated Dec. 18, 2020, for Application No. 201780041286.X, 11 pages.
Chinese Office Action dated Jul. 9, 2021, for Application No. 201780041286.X, 5 pages.
Extended European Search Report dated Oct. 28, 2020, for Application No. 2019043 7.2, 10 pages.
Indian Office Action dated Jul. 2, 2021, for Application No. 201817047713, 5 pages.
Japanese Notification of Reasons for Refusal dated Jun. 8, 2021, for Application No. 2018-568754, 4 pages.

* cited by examiner

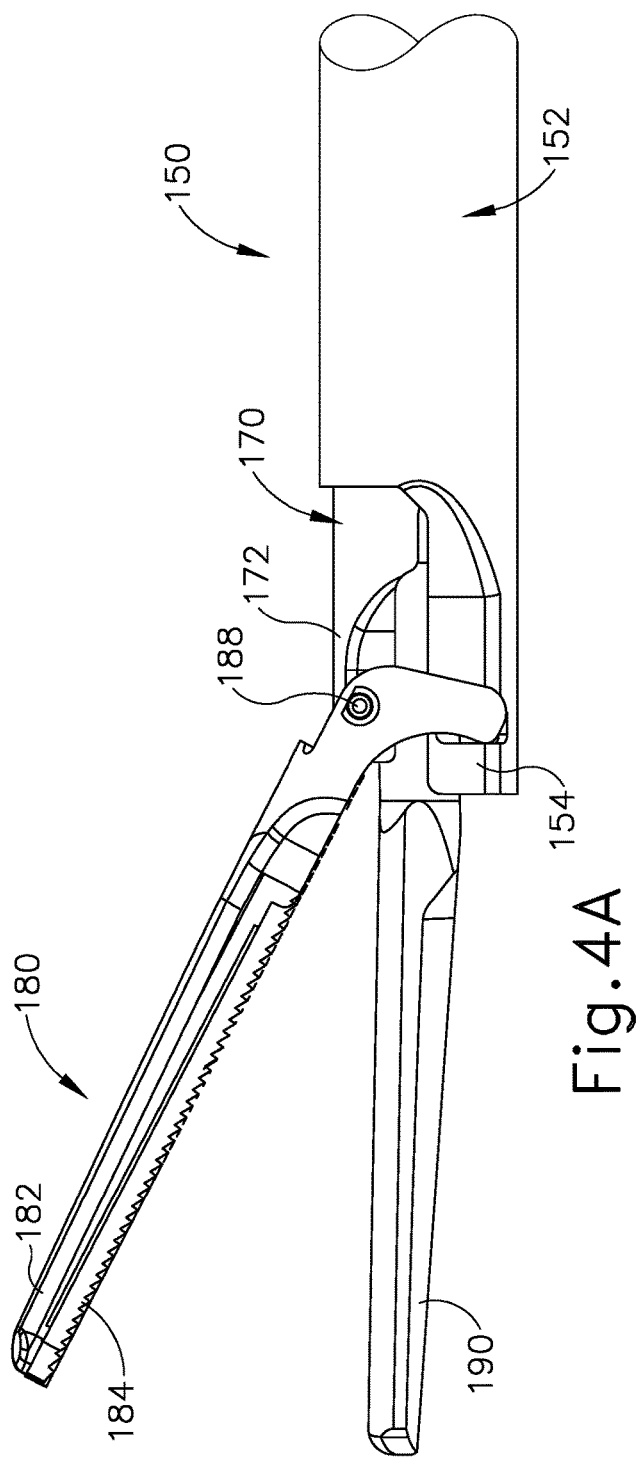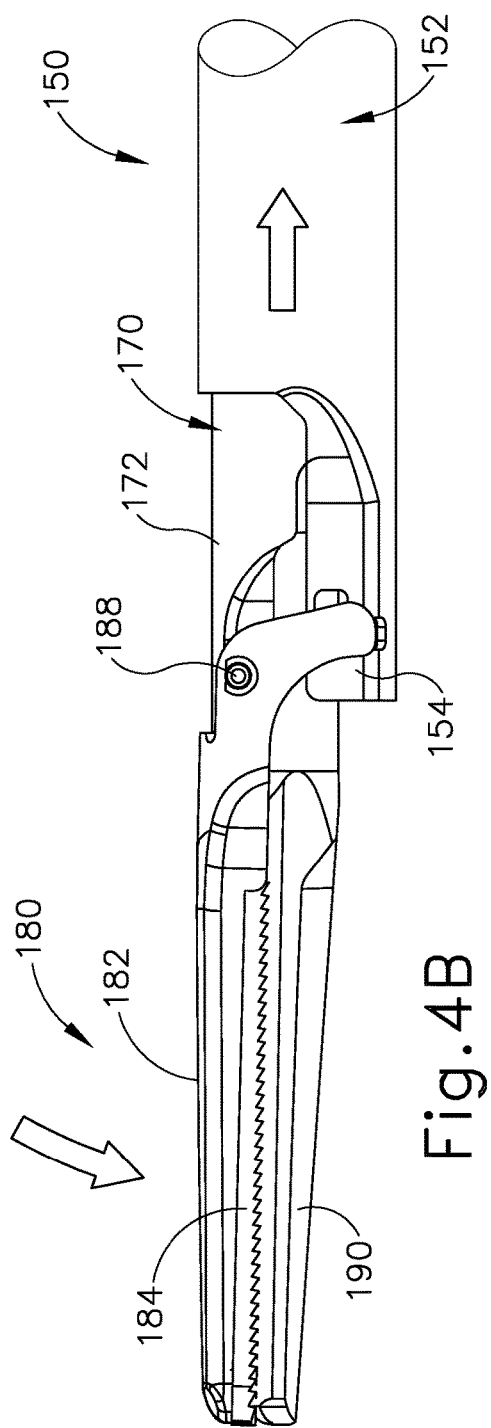
Fig.4A
Fig.4B

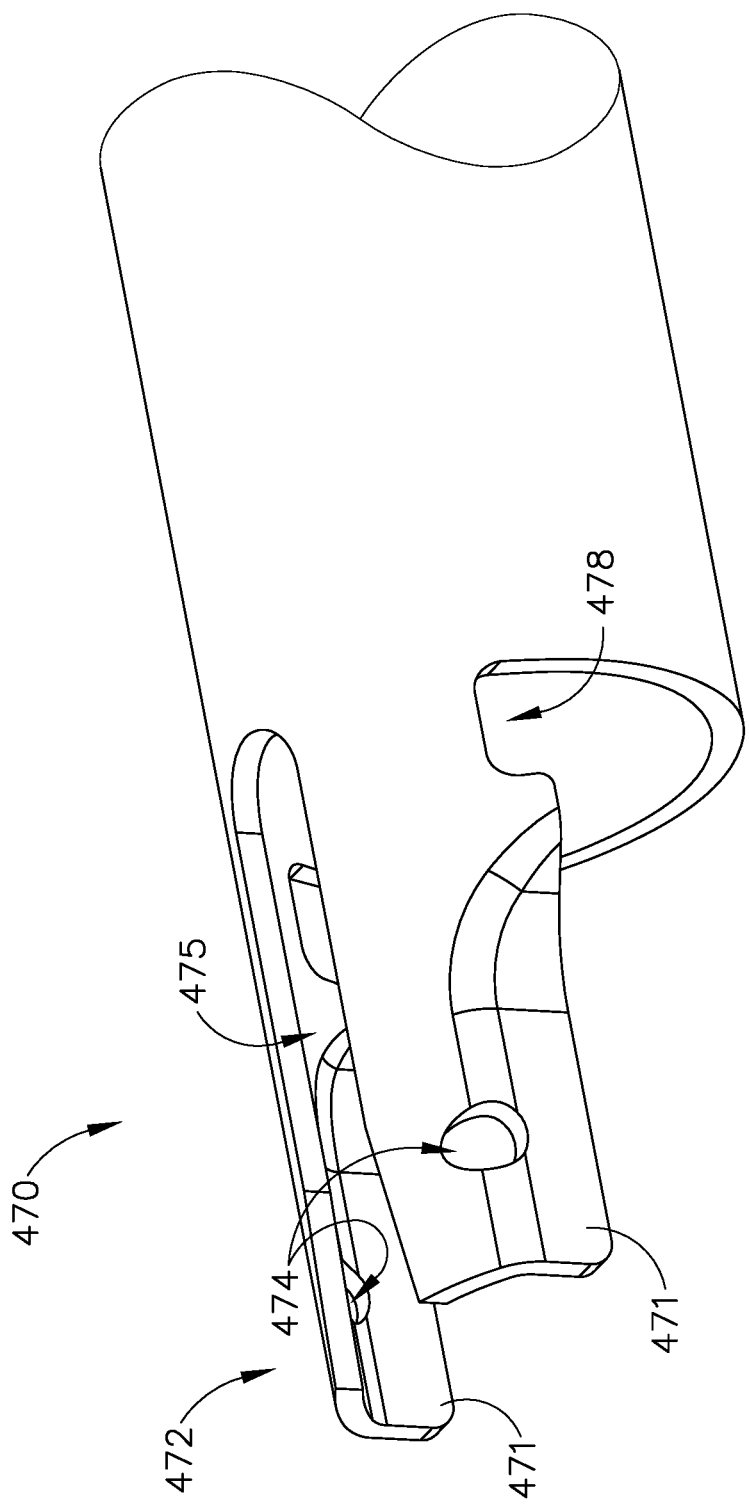

ULTRASONIC SURGICAL INSTRUMENT WITH CLAMP ARM DEFLECTION FEATURE

This application is a continuation of U.S. patent application Ser. No. 15/200,333, entitled "Ultrasonic Surgical Instrument with Clamp Arm Deflection Feature," filed Jul. 1, 2016 and published as U.S. Pub. No. 2018/000506 on Jan. 4, 2018, issued as U.S. Pat. No. 10,543,014 on Jan. 28, 2020.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While a variety of surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4A depicts a side elevational view of the end effector and the shaft assembly of FIG. 2, where the end effector is in the open configuration;

FIG. 4B depicts a side elevational view of the end effector and the shaft assembly of FIG. 2, where the end effector is in a closed configuration;

FIG. 13 depicts a perspective view of an alternative inner tube that may be readily incorporated into the shaft assembly of FIG. 2 or FIG. 6;

Figure 1:
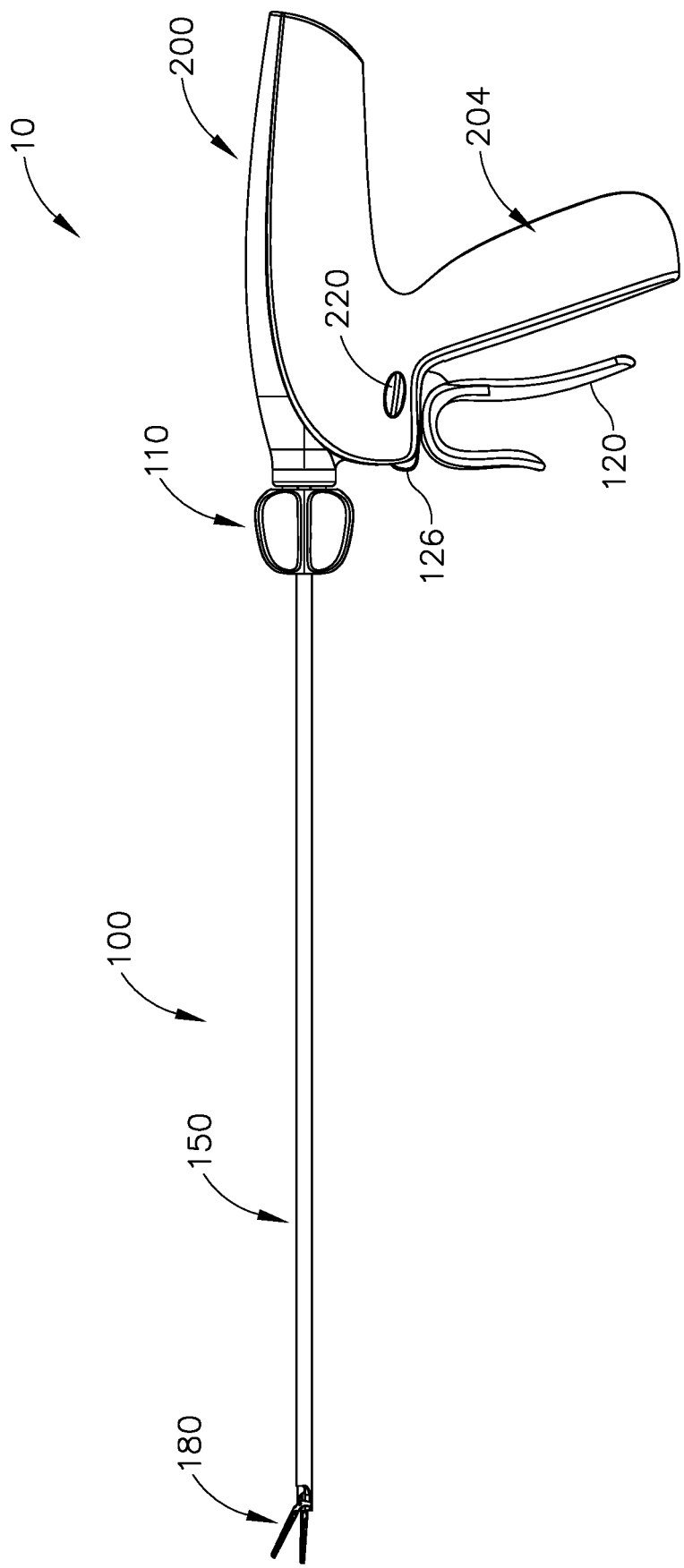
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Overview of Exemplary Ultrasonic Surgical Instrument

FIG. 1 shows an exemplary ultrasonic surgical instrument (10) that is configured to be used in minimally invasive surgical procedures (e.g., via a trocar or other small diameter access port, etc.). As will be described in greater detail below, instrument (10) is operable to cut tissue and seal or weld tissue (e.g., a blood vessel, etc.) substantially simultaneously. Instrument (10) of this example comprises a disposable assembly (100) and a reusable assembly (200). The distal portion of reusable assembly (200) is configured to removably receive the proximal portion of disposable assembly (100) to form instrument (10). However, it should be understood that reusable assembly (200) and disposable assembly (100) may alternatively be unitarily connected.

Figure 2:
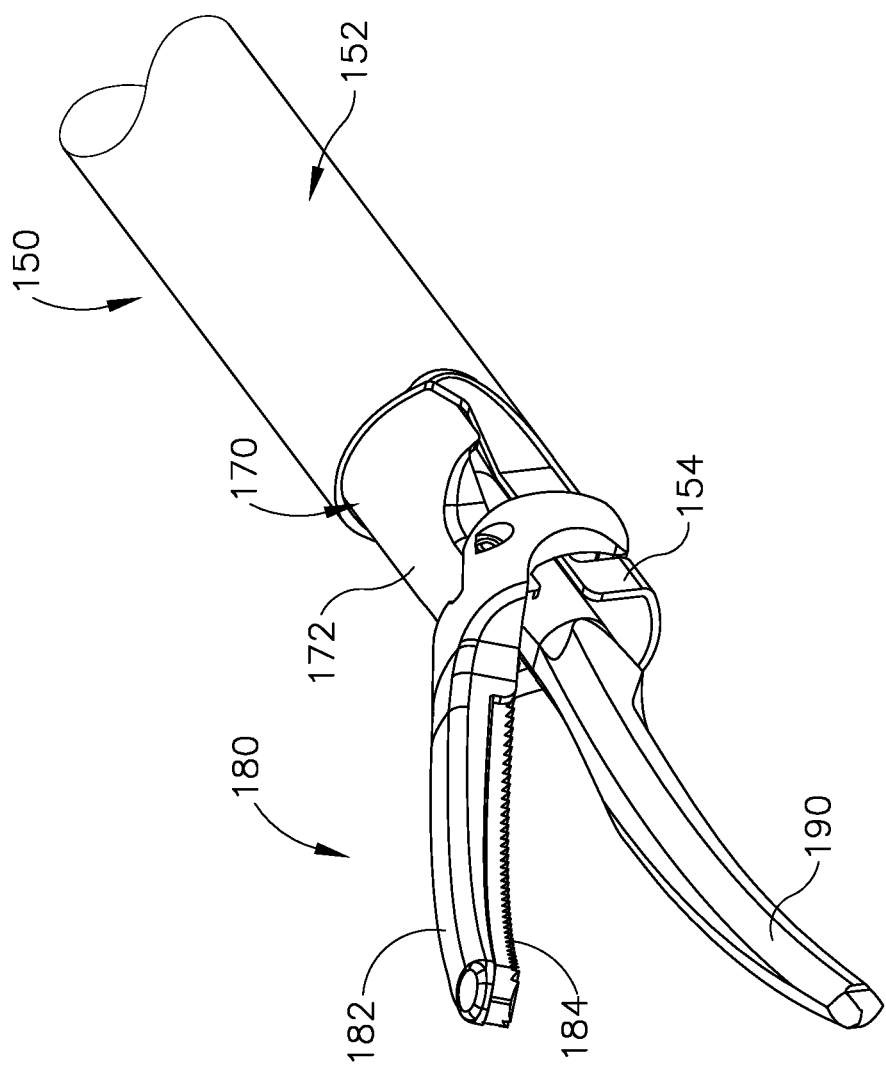
FIG. 2 depicts a perspective view of an end effector and a shaft assembly of the instrument of FIG. 1, where the end effector is in an open configuration.
Figure 3:
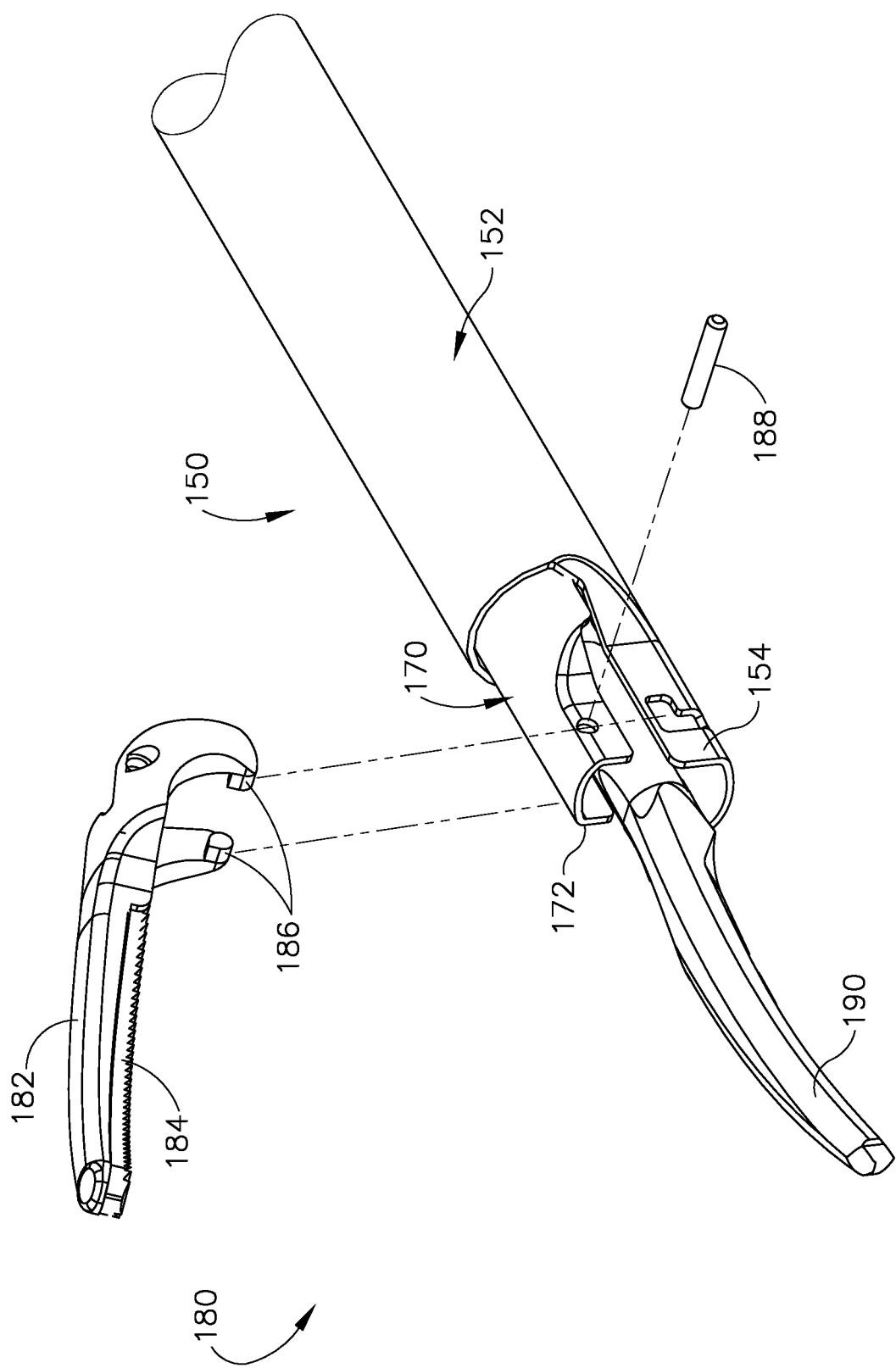
FIG. 3 depicts a partially exploded view of the end effector and the shaft assembly of FIG. 2.

Disposable assembly (100) of the present example comprises a body portion (110), a shaft assembly (150) extending distally from body portion (110), and an end effector (180) located at the distal end of shaft assembly (150). As best seen in FIGS. 2-4, end effector (180) of this example comprises a clamp arm (182) and an ultrasonic blade (190). Clamp arm (182) includes a clamp pad (184), which faces blade (190). As shown in FIGS. 3A-3B and as will be described in greater detail below, clamp arm (182) is pivotable toward and away from blade (190) to selectively compress tissue between clamp pad (184) and blade (190). As seen in FIG. 4, blade (190) is an integral feature of the distal end of an acoustic waveguide (192), which extends coaxially through tubes (152, 170), and which is configured to communicate ultrasonic vibrations to blade (190) as will be described in greater detail below.

Figure 5:
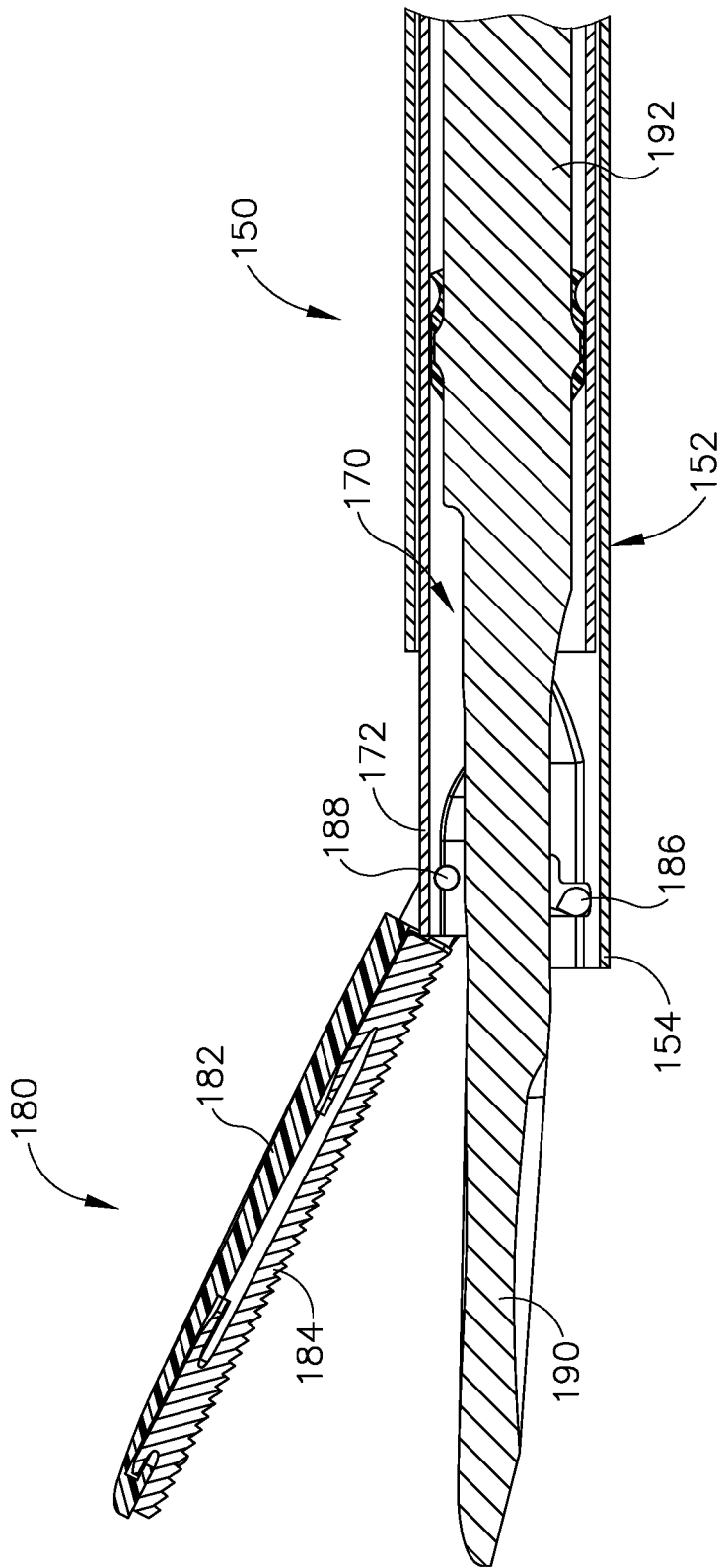
FIG. 5 depicts a side cross-sectional view of the end effector and the shaft assembly of FIG. 2, where the end effector is in the open configuration.

Shaft assembly (150) comprises an outer tube (152) and an inner tube (170). Outer tube (152) is operable to translate longitudinally relative to inner tube (170) to selectively pivot clamp arm (182) toward and away from blade (190). To accomplish this, and as best seen in FIGS. 3 and 5, integral pin features (186) of clamp arm (182) pivotally secure a first portion of clamp arm (182) to a distally projecting tongue (154) of outer tube (152); while an inserted pin (188) pivotally secures a second portion of clamp arm (182) to a distally projecting tongue (172) of inner tube (170). Thus, as can be seen in the transition from FIG. 4A to FIG. 4B, tubes (152, 170) cooperate to pivot clamp arm (182) toward blade (190) when outer tube (152) is retracted proximally relative to inner tube (170). It should be understood that clamp arm (182) may be pivoted back away from blade (190) (e.g., from the position shown in FIG. 4B to the position shown in FIG. 4A) by translating outer tube (152) distally relative to inner tube (170), in reverse of the operation shown in FIGS. 4A-4B. In an exemplary use, clamp arm (182) may be pivoted toward blade (190) to grasp, compress, seal, and sever tissue captured between clamp pad (184) and blade (190). Clamp arm (182) may be pivoted away from blade (190) to release tissue from between clamp pad (184) and blade (190); and/or to perform blunt dissection of tissue engaging opposing outer surfaces of clamp arm (182) and blade (190).

Reusable assembly (200) includes a pistol grip (204) in this example, though it should be understood that any other suitable kind of grip may be used. A trigger (120) of reusable assembly (200) is configured to pivot toward and away from pistol grip (204) to thereby translate outer tube (152), to thereby pivot clamp arm (182). Buttons (126, 220) of reusable assembly (200) are operable to activate blade (190) to cause blade (190) to vibrate at ultrasonic frequencies. In some versions, at least one button (126, 220) is also operable to activate end effector (180) to deliver RF electrosurgical energy to tissue.

Reusable assembly (200) comprises various features that are operable to activate blade (190), including a battery and an ultrasonic transducer. Reusable assembly (200) further includes features that are operable to couple the ultrasonic transducer with waveguide (192) to thereby couple the ultrasonic transducer with blade (190). In some variations, reusable assembly (200) is coupled with an external power source that provides electrical power to the ultrasonic transducer. By way of example only, such an external power source may comprise a GEN 300 sold by Ethicon Endo-Surgery, Inc. of Cincinnati, Ohio. In addition or in the alternative, the external power source may comprise a generator that is constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein.

In the present example, the distal end of blade (190) is located at a position corresponding to an anti-node associated with resonant ultrasonic vibrations communicated through waveguide (192), in order to tune the acoustic assembly to a preferred resonant frequency $f_o$ when the acoustic assembly is not loaded by tissue. When the transducer assembly is energized, the distal end of blade (190) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When the transducer assembly of the present example is activated, these mechanical oscillations are transmitted through waveguide (192) to reach blade (190), thereby providing oscillation of blade (190) at the resonant ultrasonic frequency. Thus, when tissue is secured between blade (190) and clamp pad (184), the ultrasonic oscillation of blade (190) may simultaneously sever the tissue and denature the proteins in adjacent tissue cells, thereby providing a coagulative effect with relatively little thermal spread.

In some versions, end effector (180) is operable to apply radiofrequency (RF) electrosurgical energy to tissue in addition to applying ultrasonic energy to tissue. By way of example only, end effector (180) may be configured and operable in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and/or U.S. Pat. No. 8,663,220, entitled "Ultrasonic Electrosurgical Instruments," issued Mar. 4, 2014, the disclosure of which is incorporated by reference herein.

In the present example, clamp arm (182) is actuated by translating outer tube (152) while inner tube (170) remains stationary. However, it should be understood that clamp arm (182) may instead be actuated by translating inner tube (170) while outer tube (152) remains stationary. Merely illustrative examples of such alternative forms of actuation will be described in greater detail below. Various suitable ways in which trigger (120) may be coupled with outer tube (152) or inner tube (170), in order to provide translation of outer tube (152) or inner tube (170) in response to pivoting of trigger (120) relative to pistol grip (204), will be apparent to those of ordinary skill in the art in view of the teachings herein.

In addition to the foregoing, disposable assembly (100) and/or reusable assembly (200) may be constructed and operable in accordance with at least some of the teachings of U.S. Pub. No. 2015/0245850, entitled "Ultrasonic Surgical Instrument with Removable Handle Assembly," published Sep. 3, 2015, issued as U.S. Pat. No. 10,010,340 on Jul. 3, 2018, the disclosure of which is incorporated by reference herein. In addition, or in the alternative, disposable assembly (100) and/or reusable assembly (200) may be constructed and operable in accordance with at least some of the teachings of U.S. patent application Ser. No. 14/868,574, entitled "Ultrasonic Surgical Instrument with Removable Handle Assembly," filed Sep. 29, 2015, issued as U.S. Pat. No. 10,349,967 on Jul. 16, 2019, the disclosure of which is incorporated by reference herein. Other suitable components, features, and operabilities that may be incorporated into disposable assembly (100) and/or reusable assembly (200) and variations thereof will be apparent to those of ordinary skill in the art in view of the teachings herein.

II. Exemplary Alternative End Effector and Shaft Assembly

As discussed above, clamp arm (182) of end effector (180) moves pivotally toward and away from ultrasonic blade (190). In some instances, this pivotal movement of clamp arm (182) may not allow for an adequate distribution of force to be applied to the tissue clamped between clamp arm (182) and ultrasonic blade (190). For instance, when clamp arm (182) pivots toward ultrasonic blade (190), a proximal portion of clamp arm (182) may make contact with tissue between clamp arm (182) and ultrasonic blade (190) before a distal portion of clamp arm (182) makes contact with the tissue. This inadequate distribution of force may allow for "tags" of tissue (e.g., flattened but uncut regions of tissue) to be formed, particularly at a distal end and/or proximal end of end effector (180). Thus, in some versions of instrument (10), it may be desirable to provide a mechanism that provides improved distribution of force to be applied to the tissue clamped between clamp arm (182) and ultrasonic blade (190), to reduce the occurrence of tissue tags and/or to provide severing of tissue tags.

Figure 6:
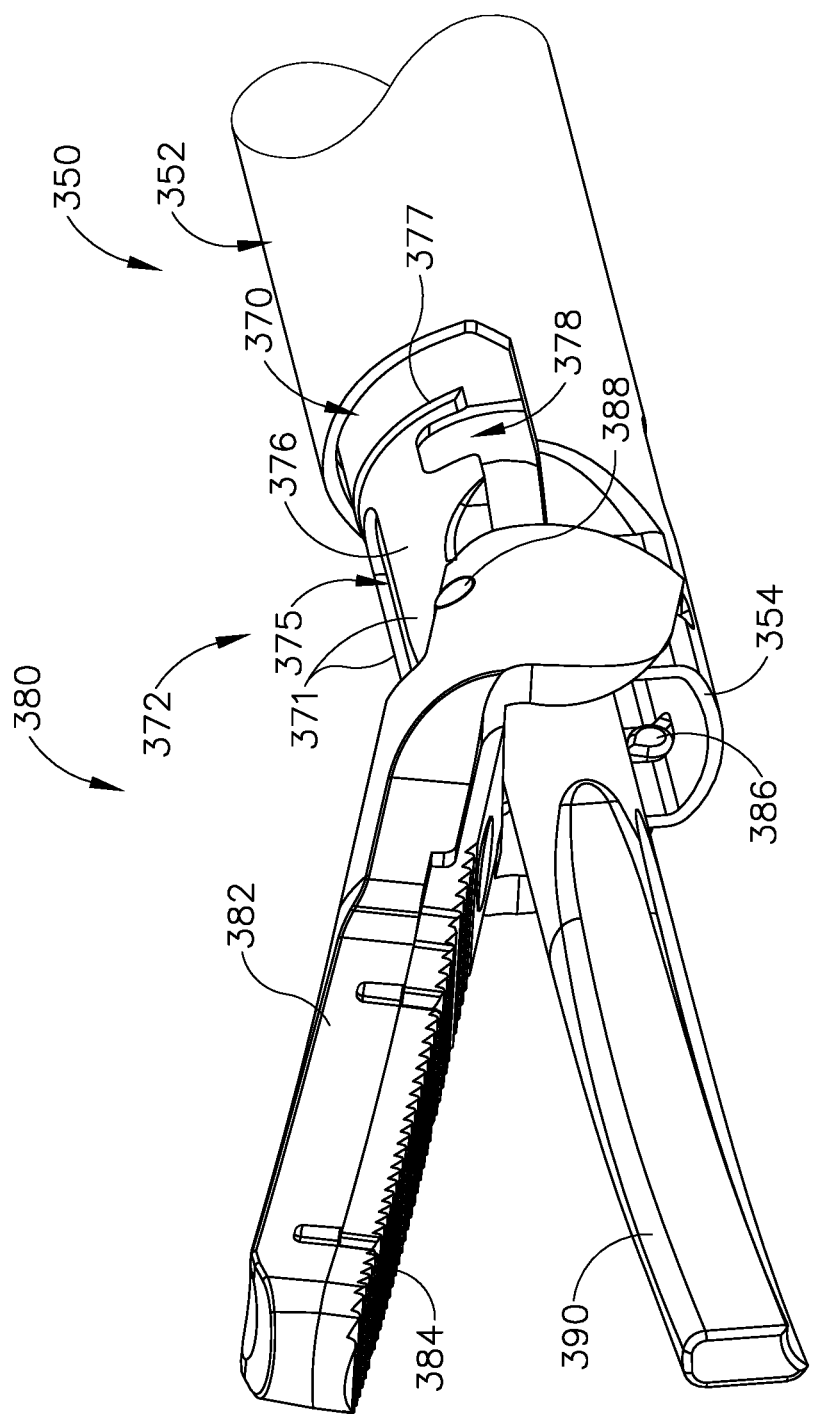
FIG. 6 depicts a perspective view of an alternative end effector and an alternative shaft assembly that may be readily incorporated into the ultrasonic surgical instrument of FIG. 1.
Figure 7:
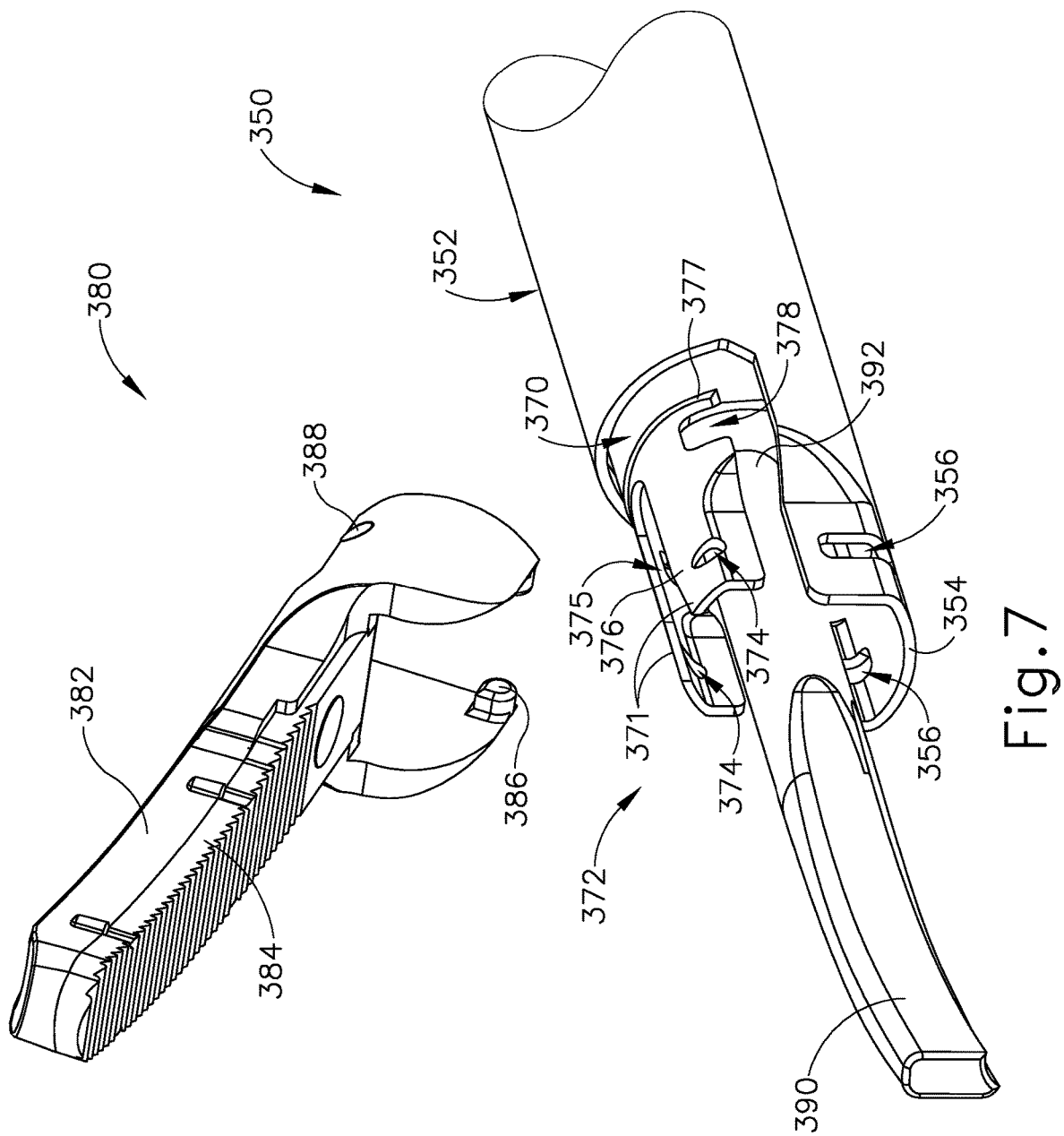
FIG. 7 depicts a partially exploded view of the end effector and the shaft assembly of FIG. 6.

FIGS. 6-7 show an alternative shaft assembly (350) and an alternative end effector (380) that may be readily incorporated into instrument (10) described above. As will be described in greater detail below, shaft assembly (350) includes features that may improve distribution of force to be applied to tissue clamped between end effector (380). End effector (380) includes a clamp arm (382) and an ultrasonic blade (390), which are substantially similar to clamp arm (182) and ultrasonic blade (190) described above, respectively with differences described below.

Clamp arm (382) includes a clamp pad (384) and a pair of integral pin features (386), substantially similar to clamp pad (184) and integral pin features (186) described above, respectively. Therefore, clamp pad (384) faces blade (390). Clamp arm (382) also includes another pair of integral pin features (388), which serve the same purpose as inserted pin (188) described above. Alternatively, integral pin features (388) may also be a single pin, insertable relative to the rest of clamp arm (382) if desired. Additionally, as will be described in greater detail below, clamp pad (384) is pivotable toward and away from blade (390) to selectively compress tissue between clamp pad (384) and blade (390). Blade (390) is an integral feature of the distal end of acoustic waveguide (392), which is substantially similar to acoustic waveguide (192) described above. Therefore, acoustic waveguide (392) extends coaxially through tubes (352, 370), and is configured to communicate ultrasonic vibrations to blade (390).

Shaft assembly (350) comprises an outer tube (352) and an inner tube (370), which are substantially similar to outer tube (152) and inner tube (170) described above, respectively, with differences described below. Therefore, outer tube (352) is operable to translate longitudinally relative to inner tube (370) to selectively pivot clamp arm (382) toward and away from blade (390). Alternatively, inner tube (370) may be translated longitudinally relative to outer tube (352) to selectively pivot clamp arm (382) toward and away from blade (390).

Inner tube (370) includes a distally projecting tongue (372) that is substantially similar to distally projecting tongue (172) described above, with differences described below. Distally projecting tongue (372) contains various features to promote elastic flexibility of distally projecting tongue (372) relative to the rest of inner tube (370). As will be described in greater detail below, this elastic flexibility may provide improved distribution of force applied to tissue clamped between clamp arm (382) and ultrasonic blade (390).

Outer tube (350) includes a distally projecting tongue (354) defining a pair of vertically elongated pin slots (356). Integral pin features (386) of clamp arm (382) pivotally couple a first portion of clamp arm (382) to distally projecting tongue (354) of outer tube (352) via vertically elongated pin slots (356). Integral pin features (386) may rotate and vertically translate within vertically elongated pin slots (356).

Distally projecting tongue (372) includes a pair of distally projecting prongs (371), each defining a respective pin hole (374). Integral pin features (388) of clamp arm (382) pivotally secure a second portion of clamp arm (382) to distally projecting tongue (372) of inner tube (370). Thus, as will be described in greater detail below, tubes (352, 370) cooperate to pivot clamp arm (382) toward blade (390) when outer tube (352) is retracted proximally relative to inner tube (370); and away from blade (390) when outer tube (353) is advanced distally relative to inner tube (370). Similar to clamp arm (182) and blade (190), clamp arm (382) may be pivoted toward blade (390) to grasp, compress, seal, and sever tissue captured between clamp pad (384) and blade (390). Clamp arm (382) may be pivoted away from blade (390) to release tissue from between clamp pad (384) and blade (390); and/or to perform blunt dissection of tissue engaging opposing outer surfaces of clamp arm (382) and blade (390).

Distally projecting prongs (371) may be made out of a sufficiently resilient material such that prongs (371) may elastically flex relative to the rest of inner tube (370) in response to an external force having a transversely oriented component. Additionally, distally projecting prongs (371) may flex back to a rested position relative to the rest of inner tube (370) (as shown in FIGS. 6-9) once the external force is removed. It should be understood prongs (371) may elastically flex from the rested position at different magnitudes depending on the magnitude of the transversely oriented component of the external force.

Distally projecting prongs (371) together define a longitudinally extending channel (375). Longitudinally extending channel (375) is open at a distal end and closed at a proximal end. Longitudinally extending channel (375) may reduce the amount of material used to form distally projecting tongue (372). Reduction in material along the length of distally projecting tongue (372) may allow the portion of prongs (371) connected to the rest of inner tube (370) to more easily flex relative to the rest of inner tube (370) when prongs (371) are exposed to an external force as compared to distally projecting tongue (172) described above. Additionally, prongs (371) may more easily flex relative to the rest of inner tube (370) at different magnitudes/angles depending on the lateral distribution of forces or other factors. In other words, prongs (371) may more easily flex relative to each other. While in the current example, longitudinally extending channel (375) has a unique geometry defined by prongs (371), any other suitable geometry may be utilized as would be apparent to one having ordinary skill in the art in view of the teachings herein.

Figure 8:
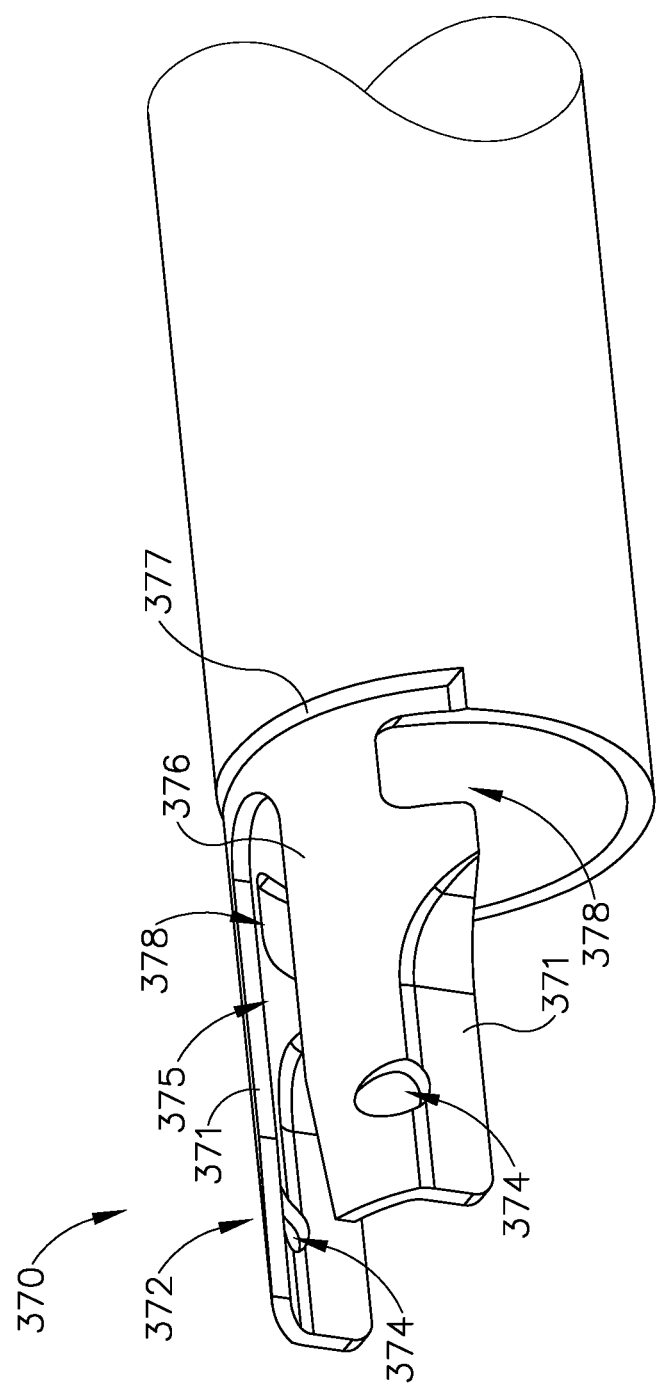
FIG. 8 depicts a perspective view of an inner tube of the shaft assembly of FIG. 6.
Figure 9:
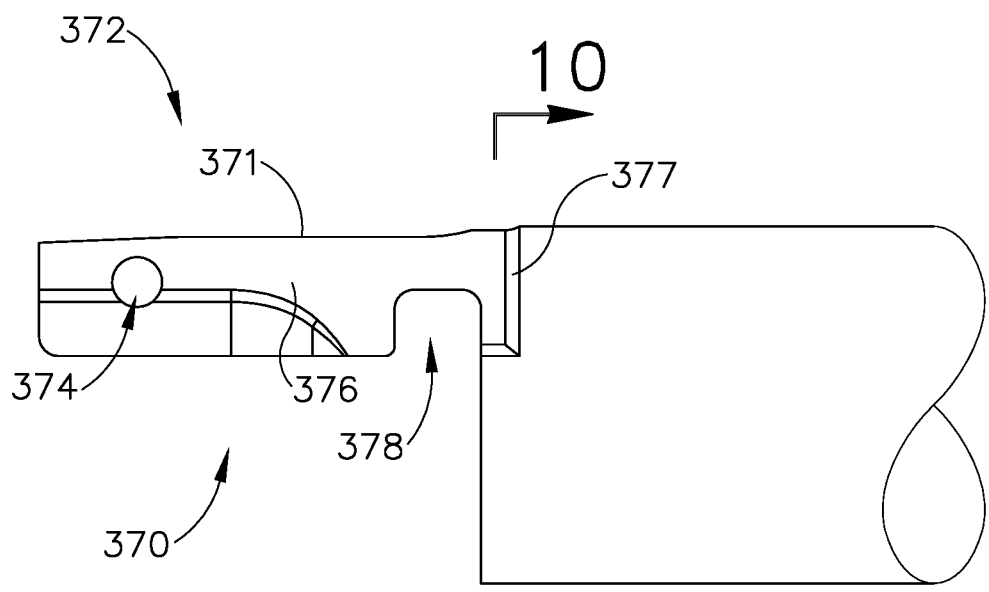
FIG. 9 depicts a side elevational view of the inner tube of FIG. 8.

As best seen in FIGS. 8-9, each distally projecting prong (371) also defines a circumferential cutout (378) located near the proximal end of distally projecting prongs (371). Similar to longitudinally extending channel (375), circumferential cutouts (378) may also reduce the amount of material used to form distally projecting tongue (372). Additionally, circumferential cutouts (378) reduces the amount of material used to connect distally projecting prongs (371) to the rest of inner tube (370). Therefore, reduction in the material connecting prongs (371) to the rest of inner tube (370) may allow prongs (371) to more easily flex relative to the rest of inner tube (370) when prongs (371) are exposed to an external force. It should be understood that the amount of material connecting distally projecting prongs (371) with the rest of inner tube (370) is still sufficient that prongs (371) will flex back to the rested position when an external force is no longer present. While in the current example, circumferential cutout (378) has a semi-rectangular geometry, any other suitable geometry may be used as would be apparent to one having ordinary skill in the art in view of the teachings herein, such as a triangular geometry.

Figure 10:
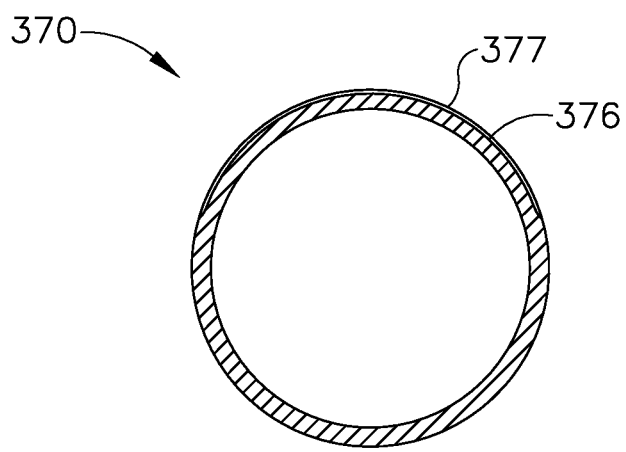
FIG. 10 depicts a cross-sectional front view of the inner tube of FIG. 8, taken along line 10-10 of FIG. 9.

Additionally, distally projecting tongue (372) contains a coined or stamped outer surface (376) extending along the outer surface of prongs (371) and proximally terminating into a partially circumferential lip (377). As best seen in FIG. 10, stamped outer surface (376) decreases the cross-sectional area of stamped portions, such as distally projecting tongue (372). In particular, stamped outer surface (376) is defined by a radius that is smaller than the radius defining the outer surface of the remainder of inner tube (370). This decrease in radius or cross-sectional area may help promote elastic flexibility of distally projecting tongue (372). While in the current example, the reduction in cross-sectional area of distally projecting tongue (372) is formed by a coining or stamping process, any other suitable process may be used as would be apparent to one having ordinary skill in the art in view of the teachings herein, such as milling, etc.

Figure 11A:
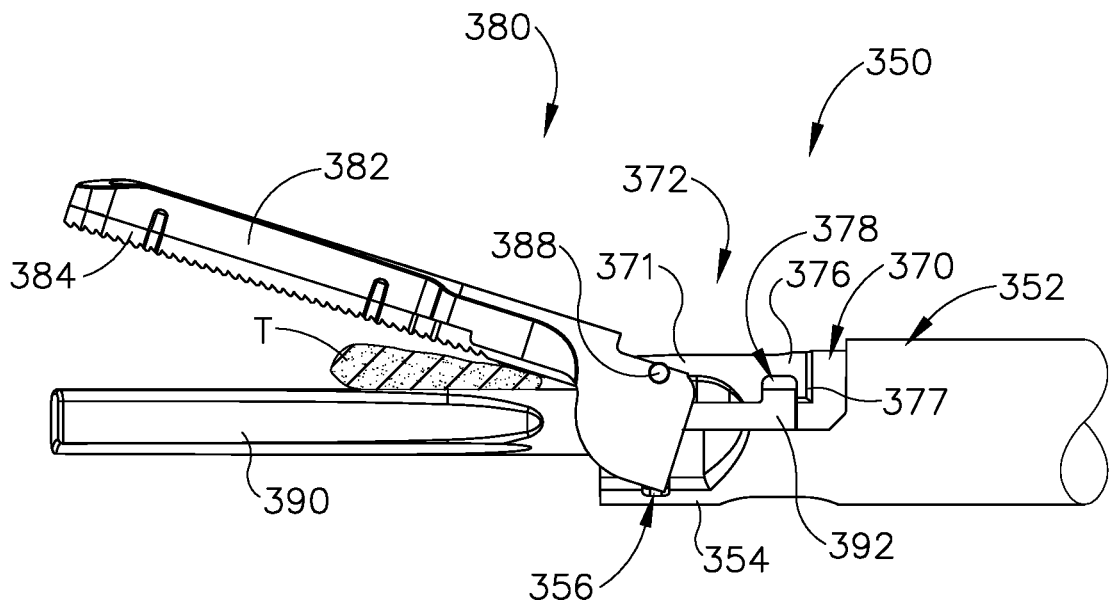
FIG. 11A depicts a side elevational view of the end effector and the shaft assembly of FIG. 6, where the end effector is in the open configuration with tissue positioned at a proximal location of the end effector.
Figure 11B:
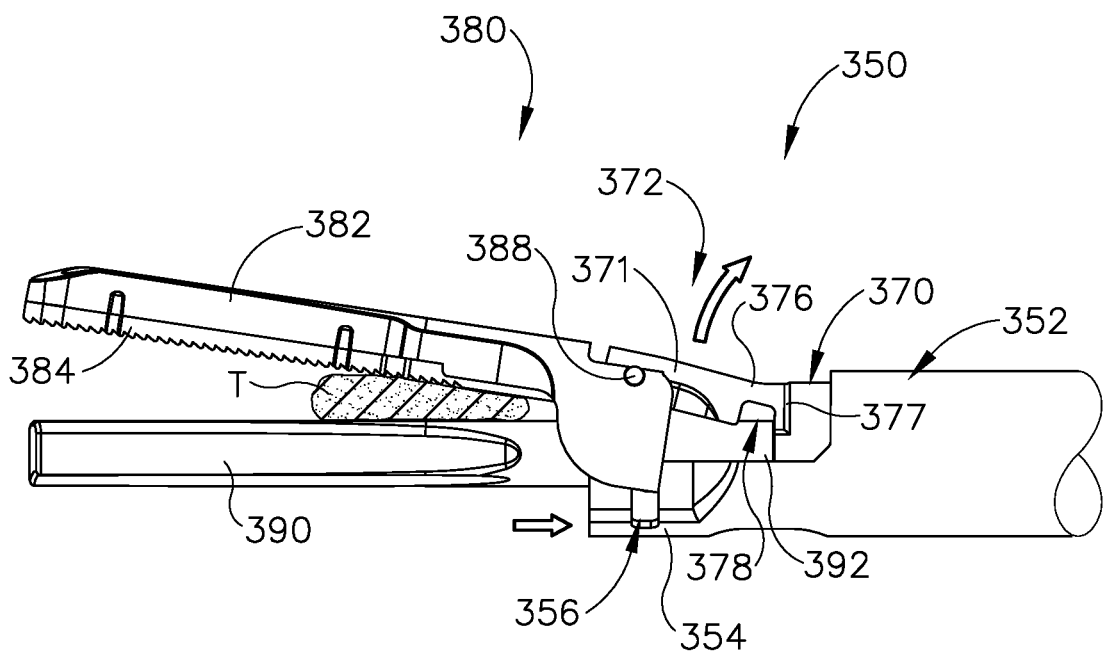
FIG. 11B depicts a side elevation view of the end effector and the shaft assembly of FIG. 6, where the end effector is in a closed configuration and is grasping tissue at a proximal location of the end effector.

FIGS. 11A-11B show shaft assembly (350) and end effector (380) being utilized in order to grasp tissue (T) along a proximal location between clamp pad (384) and blade (390). FIG. 11A shows clamp arm (382) rotated to a position just prior to making contact with tissue (T). Therefore, because tissue (T) is not in contact with clamp pad (382), tissue (T) is not imparting an external force on clamp arm (382). It should be understood that just after clamp arm (382) is rotated past the position shown in FIG. 11A toward the position shown in FIG. 11B, clamp pad (384) begins to make contact with tissue (T).

FIG. 11B shows clamp arm (382) rotated toward blade (390) and against tissue (T) due to proximal retraction of outer tube (354) relative to inner tube (370) as described above. The further clamp arm (382) rotates from the position shown in FIG. 11A toward the position shown in FIG. 11B, the greater the external force tissue (T) imparts onto clamp arm (382). It should be understood that the force imparted by tissue (T) onto clamp arm (382) has a component that is transverse to the longitudinal axis of shaft assembly (350).

The external force provided by tissue (T) making contact with clamp arm (382) transfers to distally projecting prongs (371) via integral pin features (388) and pin holes (374). Therefore, the external force provided by tissue (T) causes prongs (371) to elastically flex relative to the rest of inner tube (370), away from the longitudinal axis of shaft assembly (350). Integral pin features (388) are coupled with pin holes (374) such that integral pin features (388) travel with pin holes (374) as prongs (371) flex. Therefore, as pin holes (374) move upwardly relative to the rest of inner tube (370) via flexing of prongs (371), integral pin features (388) and clamp arm (382) also elevate upwardly within pin holes (374). In response, clamp arm (382) lifts up, causing integral pin features (386) to vertically translate within vertical pin slots (356).

The elevation of both integral pin features (386, 388) may lead to clamp arm (382) further rotating to improve longitudinal uniformity of clamp pad (384) relative to blade (390). Improved longitudinal uniformity of clamp pad (384) relative to blade (390) may improve distribution of force applied to tissue (T) clamped between clamp arm (382) and ultrasonic blade (390). In other words, the pressure applied to tissue (T) by clamp arm (382) and ultrasonic blade (390) may be more uniform along the length of the compressed tissue (T) than would be otherwise provided in the absence of flexing by prongs (371). In particular, if prongs (371) were rigid rather than flexible, the proximal portion of the compressed tissue (T) may receive substantially greater pressure than the distal portion of the compressed tissue (T). Such an uneven distribution of pressure may result in a tissue tag at the distal portion of the compressed tissue (T). Thus, by providing greater uniformity in the distribution of pressure along the length of tissue (T) that is compressed between clamp arm (382) and ultrasonic blade (390), flexible prongs (371) may reduce the occurrence of tissue tags.

It should be understood that when clamp arm (382) pivots from the position shown in FIG. 11B back to the position shown in FIG. 11A, tissue (T) no longer imparts an external force on clamp arm (382). Due to the resilient nature of distally presented tongue (372), prongs (371) flex back to the rested position shown in FIG. 11A.

Figure 12A:
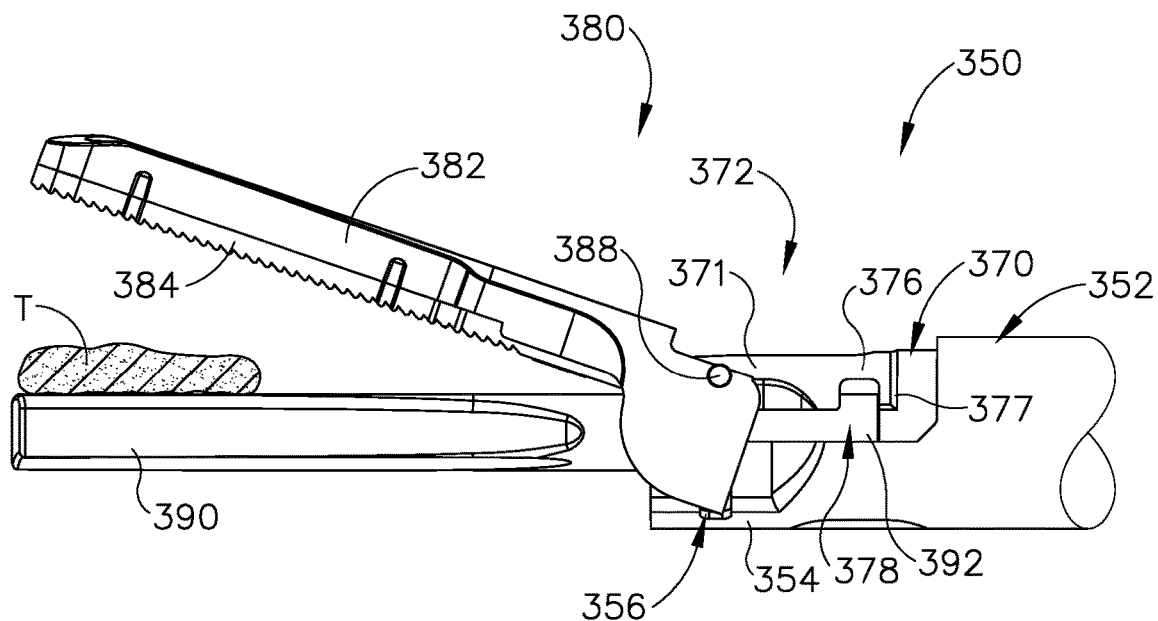
FIG. 12A depicts a side elevational view of the end effector and the shaft assembly of FIG. 6, where the end effector is in the open configuration with tissue positioned at a distal location of the end effector.
Figure 12B:
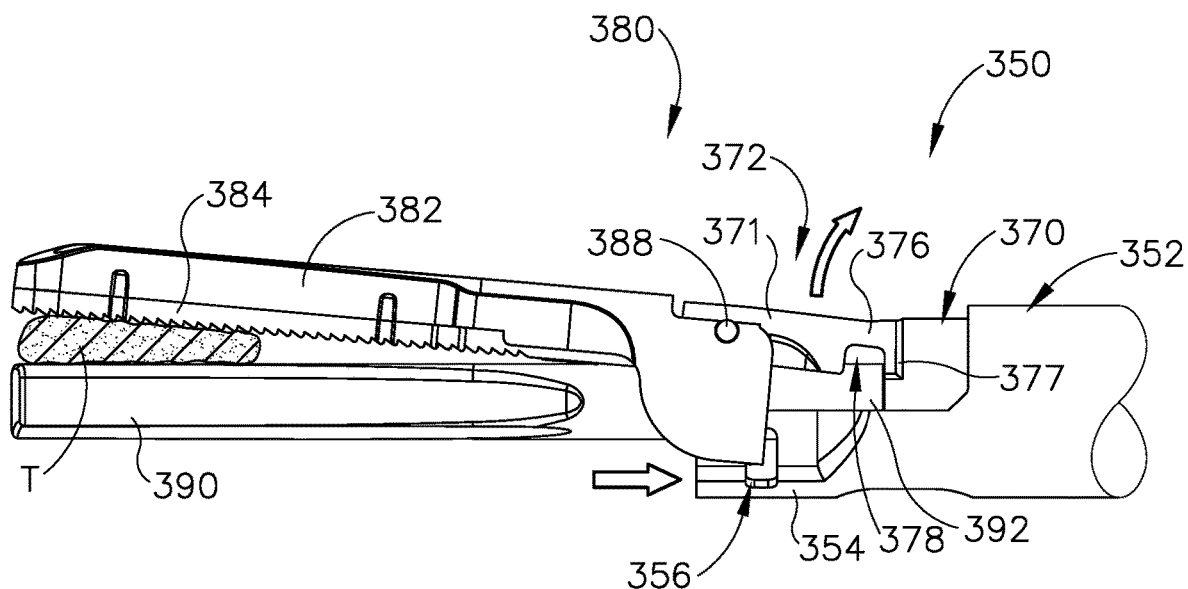
FIG. 12B depicts a side elevational view of the end effector and the shaft assembly of FIG. 6, where the end effector is in the closed configuration and is grasping tissue at a distal location of the end effector.

FIGS. 12A-12B show shaft assembly (350) and end effector (380) being utilized in order to grasp tissue (T) along a more distal location between clamp pad (384) and blade (390). FIG. 12A shows clamp arm (382) pivoted to a position similar to the position shown in FIG. 11A. However, because tissue (T) is located along a more distal location between clamp pad (384) and blade (390), clamp arm (382) will need to be further rotated toward blade (390) until clamp pad (384) makes contact with tissue (T). Therefore, because tissue (T) is not in contact with clamp pad (382), tissue (T) is not yet imparting an external force on clamp arm (382) at the stage shown in FIG. 12A.

FIG. 12B shows clamp arm (382) rotated toward blade (390) and against tissue (T) due to proximal retraction of outer tube (354) relative to inner tube (370) as described above. As mentioned above, the further clamp arm (382) rotates while making contact with tissue (T), the greater the external force tissue (T) imparts on clamp arm (382). Because clamp arm (382) makes contact with tissue (T) during a smaller range of rotation when tissue (T) is distally located between clamp pad (384) and blade (390) as compared to when tissue (T) is proximally located between clamp pad (384) and blade (390), the external force tissue (T) imparts on clamp arm (382) is also smaller. In other words, the distally positioned tissue (T) of FIGS. 12A-12B provides a fulcrum that imparts less transversely directed force on prongs (371) than the force imparted by the fulcrum provided by the proximally positioned tissue (T) of FIGS. 11A-11B.

At the stage shown in FIG. 12A, the transversely oriented component of the external force provided by tissue (T) making contact with clamp arm (382) transfers to distally projecting prongs (371) via integral pin features (388) and pin holes (374). Therefore, the external force provided by tissue (T) causes prongs (371) to elastically flex relative to the rest of inner tube (370). It should be understood that because the external force tissue (T) imparts on clamp arm (382) is smaller in the series shown in FIGS. 12A-12B as compared to the series shown in FIGS. 11A-11B, prongs (371) elastically flex at a smaller angle relative to the rest of inner tube (370).

Integral pin features (388) are coupled with pin holes (374) such that integral pin features (388) travel with pin holes (374) as prongs (371) flex. Therefore, as pin holes (374) move upwardly relative to the rest of inner tube (370) via flexing of prongs (371), integral pin features (388) and clamp arm (382) also elevate upwardly with pin holes (374). In response, clamp arm (382) lifts up, causing integral pin features (386) to vertically translate within vertical pin slots (356). The elevation of both integral pin features (386, 388) may lead to clamp arm (382) further rotating to improve longitudinal uniformity of clamp pad (384) relative to blade (390). Improved longitudinal uniformity of clamp pad (384) relative to blade (390) may improve distribution of force applied to tissue (T) clamped between clamp arm (382) and ultrasonic blade (390), which may help prevent the formation of tissue "tags" during activation of ultrasonic blade (390).

It should be understood that when clamp arm (382) pivots from the position shown in FIG. 12B back to the position shown in FIG. 12A, tissue (T) no longer imparts an external force on clamp arm (382). Due to the resilient nature of distally presented tongue (372), prongs (371) flex back to the rested position shown in FIG. 11A.

FIG. 13 shows an exemplary alternative inner tube (470) that may be readily incorporated into shaft assembly (150, 350). Inner tube (470) includes a distally projecting tongue (472) that is substantially similar to distally projecting tongue (372) described above, with differences described below. Therefore, distally projecting tongue (472) contains various features to promote elastic flexibility of distally projecting tongue (472) relative to the rest of inner tube (470).

Distally projecting tongue (472) includes a pair of distally projecting prongs (471), each defining a respective pin hole (474), which may pivotally couple to integral pin features (388) of clamp arm (382) or pin (188) of clamp arm (182). Distally projecting prongs (471) may be made out of a sufficiently resilient material, similar to prongs (371) described above, such that prongs (471) may elastically flex relative to the rest of inner tube (470) in response to an external force having a transversely oriented component.

Distally projecting prongs (471) together define a longitudinally extending channel (475) similar to longitudinally extending channel (375) described above. Longitudinally extending channel (475) may provide the same advantages as longitudinally extending channel (375) described above. While in the current example, longitudinally extending channel (475) has a unique geometry defined by prongs (471), any other suitable geometry may be utilized as would be apparent to one having ordinary skill in the art in view of the teachings herein.

Each distally projecting prong (471) also defines a circumferential cutout (478) located near the proximal end of distally projecting prongs (471), similar to circumferential cutout (378) described above. Therefore, circumferential cutout (478) may provide the same advantages as circumferential cutout (378) described above. While in the current example, circumferential cutout (478) has a semi-rectangular geometry, any other suitable geometry (e.g., triangular geometry, etc.) may be used as would be apparent to one having ordinary skill in the art in view of the teachings herein.

Distally projecting tongue (472) is different that distally projecting tongue (372) described above in that distally projecting tongue (472) lacks any type of coined or stamped outer surface. While in the current example, distally projecting tongue (472) does not include a coined or stamped outer surface, distally projecting tongue (472) could include a coined or stamped outer surface and instead omit a circumferential cutout (378). Therefore, it should be understood that any number of selected features from distally projecting tongue (370) may be combined with features of tongue (472) in order to promote flexibility of the distal end of inner tube (470) as would be apparent to one having ordinary skill in the art in view of the teachings herein.

Figure 14:
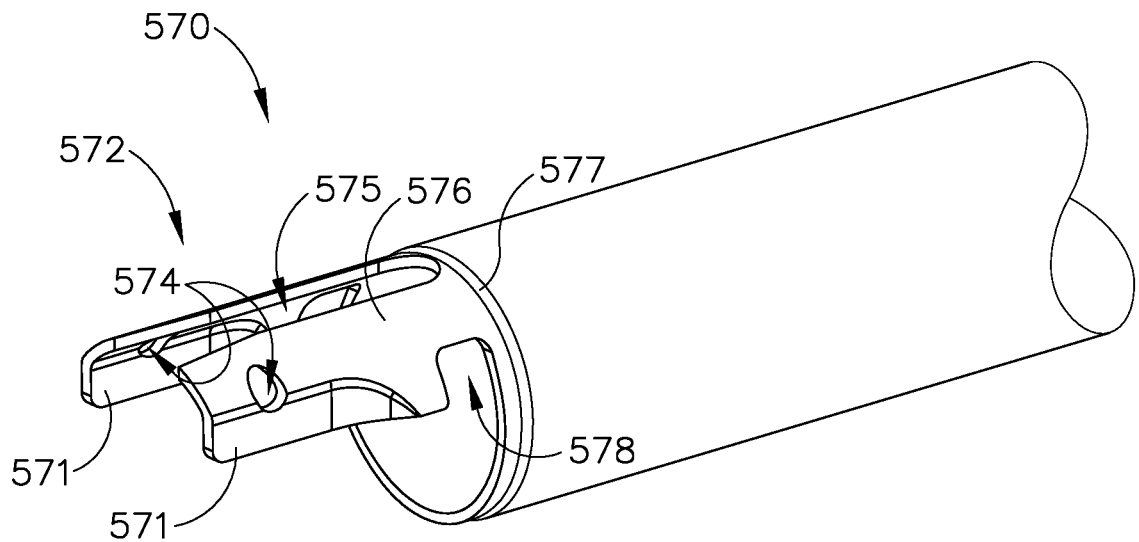
FIG. 14 depicts a perspective view of another alternative inner tube that may be readily incorporated into the shaft assembly of FIG. 2 or FIG. 6.
Figure 15:
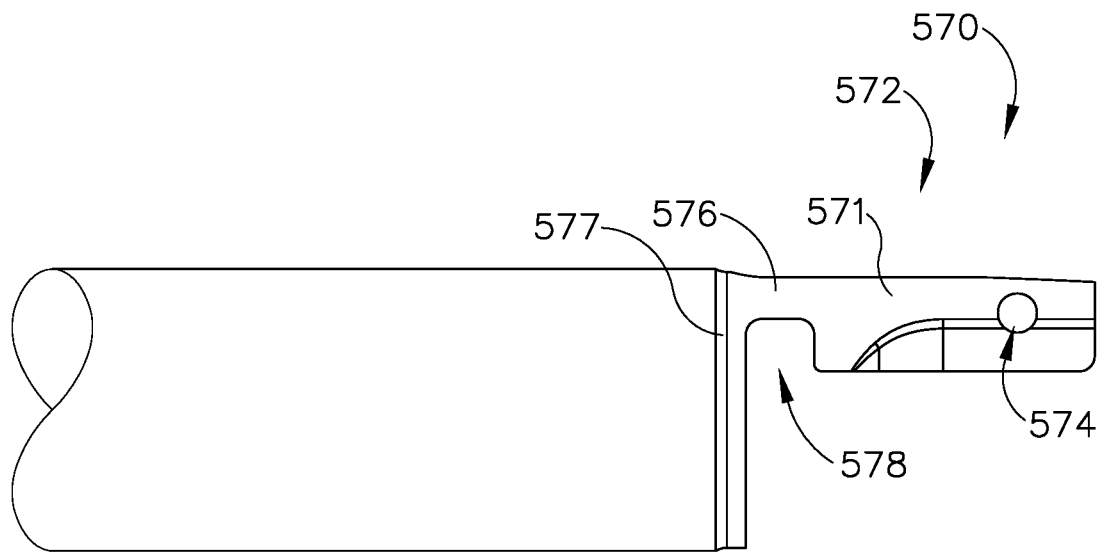
FIG. 15 depicts a side elevational view of the inner tube of FIG. 14.

FIGS. 14-15 show another exemplary alternative inner tube (570) that may be readily incorporated into shaft assembly (150, 350). Inner tube (570) includes a distally projecting tongue (572) that is substantially similar to distally projecting tongue (372, 472) described above, with differences described below. Therefore, distally projecting tongue (572) contains various features to promote elastic flexibility of distally projecting tongue (572) relative to the rest of inner tube (570).

Distally projecting tongue (572) includes a pair of distally projecting prongs (571), each defining a respective pin hole (574), which may pivotally couple to integral pin features (388) of clamp arm (382) or pin (188) of clamp arm (182). Distally projecting prongs (571) may be made out of a sufficiently resilient material, similar to prongs (371, 471) described above, such that prongs (571) may elastically flex relative to the rest of inner tube (570) in response to an external force.

Distally projecting prongs (571) together define a longitudinally extending channel (575) that is similar to longitudinally extending channel (375, 475) described above. Longitudinally extending channel (575) may provide the same advantages as longitudinally extending channel (375, 475) described above. While in the current example, longitudinally extending channel (575) has a unique geometry defined by prongs (571), any other suitable geometry may be utilized as would be apparent to one having ordinary skill in the art in view of the teachings herein.

Each distally projecting prong (571) also defines a circumferential cutout (578) located near the proximal end of distally projecting prongs (571), similar to circumferential cutout (378, 478) described above. Therefore, circumferential cutout (578) may provide the same advantages as circumferential cutout (378, 478) described above. While in the current example, circumferential cutout (578) has a semi-rectangular geometry, any other suitable geometry (e.g., a triangular geometry, etc.) may be used as would be apparent to one having ordinary skill in the art in view of the teachings herein.

Distally projecting tongue (572) contains a coined or stamped outer surface (576) extending along the outer surface of prongs (571) and proximally terminating into a circumferential lip (577). Unlike circumferential lip (377) and stamped outer surface (376), circumferential lip (577) and stamped outer surface (576) extend about the full circumference of inner tube (570). Stamped outer surface (576) may provide similar functionality and/or benefits as stamped outer surface (376) described above.

While flexing tongues (372, 472, 572) are described herein as being part of inner tubes (370, 470, 570), it should be understood that tongue (154, 354) of outer tube (152, 352) may have the same flexing features of tongues (372, 472, 572) as described above. In some versions where tongue (154, 354) is configured to flex as described herein, inner tube (170) may have a non-flexing tongue (172). In some other tongue (154, 354) is configured to flex as described herein, inner tube (370, 470, 570) may have a flexing tongue (372, 472, 572).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a shaft assembly comprising: (i) a first tube, (ii) a second tube coaxially disposed within the first tube, wherein one of the first tube or the second tube is configured to translate relative to the other of the first tube or the second tube, and (iii) a distally projecting tongue fixed to either the first tube or the second tube; and (b) an end effector comprising: (i) an ultrasonic blade extending from the shaft assembly, and (ii) a clamp arm pivotally coupled to the distally projecting tongue of the shaft assembly, wherein the clamp arm is configured to pivot toward and away from the ultrasonic blade in response to relative translation between the first and second tubes, wherein the distally projecting tongue is configured to flex relative to the first tube and the second tube in response to the clamp arm grasping tissue Example 2

The apparatus of Example 1, wherein the distally projecting tongue further comprises a pair of prongs configured to pivotally couple with the clamp arm.

Example 3

The apparatus of Example 2, wherein the pair of prongs define a longitudinally extending channel.

Example 4

The apparatus of any one or more of Examples 1 through 3, wherein the distally projecting tongue defines a pair of circumferential cutouts.

Example 5

The apparatus of Example 4, wherein the circumferential cutouts are located adjacent to a distal end of either the first tube or the second tube.

Example 6

The apparatus of one or more of Examples 1 through 5, wherein the distally projecting tongue has an outer surface defined by a first radius, wherein the first tube or the second tube fixed to the distally projecting tongue has an outer surface defined by a second radius, wherein the first radius is smaller than the second radius.

Example 7

The apparatus of Example 6, wherein the distally projecting tongue has a coined outer surface.

Example 8

The apparatus of Example 7, wherein the coined outer surface terminates into a lip, wherein the lip transitions from the first cross-sectional area to the second cross-sectional area.

Example 9

The apparatus of Example 8, wherein the lip extends along only a portion of the circumference of the first tube or second tube fixed to the distally projecting tongue.

Example 10

The apparatus of one or more of Examples 8 through 9, wherein the lip extends along the full circumference of the first tube or second tube fixed to the distally projecting tongue.

Example 11

The apparatus of one or more of Examples 1 through 10, wherein the clamp arm further comprises a first pair of integral pins and a second pair of integral pins, wherein the first pair of integral pins are configured to pivotally couple the clamp arm with the protrusions of the distally projecting tongue.

Example 12

The apparatus of one or more of Examples 1 through 11, wherein the clamp arm further comprises a clamp pad, wherein the clamp pad is positioned to face the ultrasonic blade.

Example 13

The apparatus of one or more of Examples 1 through 12, wherein the first tube comprises a pair of vertically elongated slots configured to couple with the clamp arm.

Example 14

The apparatus of Example 13, wherein the clamp arm comprises a pair of integral pins, wherein the integral pins are configured to pivot within the vertically elongated slots, wherein the integral pins are configured to translate within the vertically elongated slots.

Example 15

The apparatus of one or more of Examples 13 through 14, wherein the integral pins are configured to translate within the vertically elongated slots in response to the distally projecting tongue flexing relative to the first tube and the second tube.

Example 16

An apparatus comprising: (a) a clamp arm actuation assembly; (b) a shaft assembly comprising: (i) a first shaft, (ii) a second shaft, wherein the first shaft is slidably disposed within the second shaft, wherein one of the first shaft or the second shaft is configured to translate relative to the other of the first shaft or the second shaft in response to actuation of the clamp arm actuation assembly, and (iii) a tongue projecting distally from the second shaft; and (c) an end effector comprising: (i) an ultrasonic blade extending from the shaft assembly, and (ii) a clamp arm pivotally coupled to the tongue, wherein the clamp arm is configured to pivot toward and away from the ultrasonic blade in response to actuation of the clamp arm actuation assembly, wherein the tongue is configured to flex relative to the second shaft in response to the clamp arm compressing tissue against the ultrasonic blade.

Example 17

The apparatus of Example 16, wherein the distally projecting tongue further comprises a first prong and a second prong, wherein the first prong defines a first circumferential cutout, wherein the second prong defines a second circumferential cutout.

Example 18

The apparatus of Example 17, wherein the first circumferential cutout and the second circumferential cutout are adjacent to the second shaft.

Example 19

The apparatus of one or more of Examples 16 through 18, wherein the distally projecting tongue comprises a coined outer surface.

Example 20

An apparatus comprising: (a) a clamp arm actuation assembly; (b) a shaft assembly comprising: (i) a first shaft, (ii) a second shaft, wherein the first shaft is slidably disposed within the second shaft, wherein one of the first shaft or the second shaft is configured to translate relative to the other of the first shaft or the second shaft in response to actuation of the clamp arm actuation assembly, and (iii) a tongue projecting distally from the second shaft, wherein the tongue comprises: (A) a first prong, (B) a second prong, wherein the first prong and the second prong define a longitudinal channel, and (C) a coined outer surface extending along the first prong and the second prong; and (c) an end effector comprising: (i) an ultrasonic blade extending from the shaft assembly, and (ii) a clamp arm pivotally coupled to the tongue, wherein the clamp arm is configured to pivot toward and away from the ultrasonic blade in response to actuation of the clamp arm actuation assembly, wherein the tongue is configured to flex relative to the second shaft in response to the clamp arm compressing tissue against the ultrasonic blade.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:
1. An apparatus, comprising:
(a) an end effector, wherein the end effector comprises:
    (i) an ultrasonic blade, and
    (ii) a clamp arm configured to pivot toward and away from the ultrasonic blade; and
(b) a shaft assembly extending proximally from the end effector, wherein the shaft assembly comprises:
    (i) a first tube, wherein the clamp arm is pivotable relative to the first tube,
    (ii) a second tube coaxially aligned with the first tube, wherein the first tube or the second tube is configured to translate relative to the other of the first tube or the second tube, wherein the clamp arm is configured to pivot toward and away from the ultrasonic blade in response to relative translation between the first tube and the second tube, wherein the second tube comprises:
        (A) a distally projecting tongue, wherein the clamp arm is pivotably coupled to the distally projecting tongue such that the distally projecting tongue is configured to flex relative to the first tube and a proximal portion of the second tube in response to the clamp arm grasping tissue,
        (B) a circumferential lip extending around a first full circumference of the second tube, wherein the distally projecting tongue extends distally away from the circumferential lip, and
        (C) a stamped surface having a reduced cross-sectional area compared to the circumferential lip, wherein the stamped surface extends around a second full circumference of the second tube.

2. The apparatus of claim 1, wherein the distally projecting tongue is formed of a resilient material.

3. The apparatus of claim 1, wherein the distally projecting tongue further comprises a pair of distally projecting prongs.

4. The apparatus of claim 3, wherein the pair of distally projecting prongs are configured to elastically flex relative to each other.

5. The apparatus of claim 3, wherein the pair of distally projecting prongs further define a longitudinally extending channel.

6. The apparatus of claim 5, wherein the longitudinally extending channel terminates proximally adjacent to the circumferential lip.

7. The apparatus of claim 3, wherein the pair of distally projecting prongs each define a pin hole, wherein the clamp arm is pivotably coupled with the distally projecting prongs via the pin holes.

8. The apparatus of claim 7, further comprising a handle assembly, wherein the shaft assembly extending proximally into the handle assembly.

9. The apparatus of claim 3, wherein the pair of distally projecting prongs each define a circumferential cutout.

10. The apparatus of claim 9, wherein the circumferential cutouts comprise a semi-rectangular geometry.

11. The apparatus of claim 9, wherein each circumferential cutout defined by the pair of distally projecting prongs are adjacent to the circumferential lip.

12. The apparatus of claim 1, wherein the second full circumference is located, in its entirety, distally relative to the first full circumference.

13. The apparatus of claim 1, further comprising a handle assembly, wherein a proximal portion of the shaft assembly is coupled to the handle assembly.

14. The apparatus of claim 13, wherein the handle assembly further comprises a trigger configured to drive relative translation between the first tube and the second tube.

15. The apparatus of claim 14, wherein the trigger is pivotable relative to a remainder of the handle assembly.

16. The apparatus of claim 1, wherein the shaft assembly further comprises an ultrasonic waveguide extending proximally from the ultrasonic blade.

17. The apparatus of claim 1, wherein the clamp arm further comprises a clamp pad.

18. An apparatus, comprising:
(a) an end effector, wherein the end effector comprises:
 (i) an ultrasonic blade, and
 (ii) a clamp arm configured to pivot toward and away from the ultrasonic blade; and
(b) a shaft assembly extending proximally from the end effector, wherein the shaft assembly comprises:
 (i) a first tube, wherein the clamp arm is pivotably coupled to the first tube,
 (ii) a second tube coaxially aligned with the first tube, wherein the first tube or the second tube is configured to translate relative to the other of the first tube or the second tube, wherein the clamp arm is configured to pivot toward and away from the ultrasonic blade in response to relative translation between the first tube and the second tube, wherein the second tube comprises:
  (A) a proximal portion having a first thickness, wherein a section of the proximal portion having the first thickness extends about a first full circumference of the second tube,
  (B) a distal portion comprising a second thickness smaller than the first thickness,
  (C) a circumferential lip extending about a second full circumference of the second tube, wherein the circumferential lip is entirely located between the proximal portion and the distal portion, and
  (D) a distally projecting tongue associated with the distal portion of the second tube, wherein the clamp arm is pivotably coupled to the distally projecting tongue such that the distally projecting tongue is configured to flex relative to the first tube and a remainder of the second tube in response to the clamp arm grasping tissue.

19. The apparatus of claim 18, wherein the distally projecting tongue comprises a pair of distally projecting prongs.

20. An apparatus, comprising:
(a) an end effector, wherein the end effector comprises:
 (i) an ultrasonic blade, and
 (ii) a clamp arm configured to pivot toward and away from the ultrasonic blade;
(b) a shaft assembly extending proximally from the end effector, wherein the shaft assembly comprises:
 (i) a first tube, wherein the clamp arm is pivotably coupled to the first tube,
 (ii) a second tube coaxially aligned with the first tube, wherein the first tube or the second tube is configured to translate relative to the other of the first tube or the second tube, wherein the clamp arm is configured to pivot toward and away from the ultrasonic blade in response to relative translation between the first tube and the second tube, wherein the second tube comprises:
  (A) a circumferential lip extending about a first full circumference of the second tube, wherein a first portion of the second tube extends proximally from the circumferential lip and comprises a first thickness, wherein a second portion of the second tube extends distally from the circumferential lip and comprises a second thickness which is smaller than the first thickness, wherein the second portion of the tube extends about a second full circumference of the second tube, and
  (B) a distally projecting tongue extending distally from the circumferential lip of the second tube, wherein the clamp arm is pivotably coupled to the distally projecting tongue such that the distally projecting tongue is configured to flex relative to the first tube and a remainder of the second tube in response to the clamp arm grasping tissue.

* * * * *